(12) United States Patent
Robertson et al.

(10) Patent No.: US 7,397,036 B2
(45) Date of Patent: Jul. 8, 2008

(54) APPARATUS AND METHOD FOR MEASURING THE SIGNAL FROM A FLUORESCING NANODROP CONTAINED BY SURFACE TENSION

(75) Inventors: Charles William Robertson, Rockland, DE (US); Joel Bruce Hansen, Newark, DE (US)

(73) Assignee: NanoDrop Technologies, LLC, Wilmington, DE (US)

( * ) Notice: Subject to any disclaimer, the term of this patent is extended or adjusted under 35 U.S.C. 154(b) by 0 days.

(21) Appl. No.: 11/888,918

(22) Filed: Aug. 2, 2007

(65) Prior Publication Data
US 2008/0002181 A1 Jan. 3, 2008

Related U.S. Application Data

(63) Continuation of application No. PCT/US2006/004406, filed on Feb. 9, 2006.

(60) Provisional application No. 60/652,487, filed on Feb. 11, 2005.

(51) Int. Cl.
*G01J 3/28* (2006.01)
(52) U.S. Cl. ........................ 250/368; 250/364
(58) Field of Classification Search ............... 250/338.1
See application file for complete search history.

(56) References Cited

U.S. PATENT DOCUMENTS

| | | | |
|---|---|---|---|
| 5,422,719 A | 6/1995 | Goldstein | |
| 5,500,536 A | 3/1996 | Nogami et al. | |
| 5,678,751 A | 10/1997 | Buchanan et al. | |
| 5,922,285 A | 7/1999 | Melendez et al. | |
| 6,313,471 B1 | 11/2001 | Glebeler et al. | |
| 6,574,406 B2 | 6/2003 | Ainslie et al. | |
| 6,628,382 B2 * | 9/2003 | Robertson | 356/246 |
| 6,809,826 B2 * | 10/2004 | Robertson | 356/440 |
| 6,836,332 B2 * | 12/2004 | Mosley et al. | 356/436 |
| 2006/0109467 A1 * | 5/2006 | Evans | 356/432 |
| 2006/0109468 A1 * | 5/2006 | Evans | 356/432 |
| 2008/0028854 A1 * | 2/2008 | Evans | 73/431 |

OTHER PUBLICATIONS

"Principles of Fluorescence Spectroscopy", Joseph R. Lakewitz, 1999, Kluwer Academic/Plenum Publishers, 233 Spring St, New York, NY 10013, pp. 1-9.

* cited by examiner

*Primary Examiner*—David P. Porta
*Assistant Examiner*—David S Baker
(74) *Attorney, Agent, or Firm*—Edward J. Kaliski (57) ABSTRACT

Apparatus and method for measuring the fluorescence of nanodrop liquid samples is described in which the sample is held by surface tension between two anvil surfaces. Each anvil surface has an embedded optical fiber with its end finished flush with the surface in the containment area wetted by the sample with the fiber in line. Sample excitation is provided from the side of the sample remote from the containment area. By selection of the fiber transmission numeric aperture the impact of exciting and ambient light on the measurement is minimized. A method of virtual filtering is taught in which any ambient or exciting light that does impinge on the measuring sensor is corrected by subtracting a scaled representation of the source from the measurement. The method and apparatus is capable of detecting 1 femtomole of sodium fluorescein in 1 microliter of TE buffer.

14 Claims, 11 Drawing Sheets

Load

Figure 5A

Compress

Figure 5B

Measure

APPARATUS AND METHOD FOR MEASURING THE SIGNAL FROM A FLUORESCING NANODROP CONTAINED BY SURFACE TENSION

FIELD OF THE INVENTION

The invention relates to the field of spectrofluorometry and its use in quantitating and or characterizing liquids and solutions. More particularly it relates to the fluorometry of nanodrop liquids and even more particularly to such nanodrops contained by surface tension.

BACKGROUND OF THE INVENTION

Low sample volume instruments that work in the range of 2 microliters or less are particularly useful in the quantitation of biotechnology samples including nucleic acids, proteins and drugs and any other liquid samples where it is desirable to keep the volume of the sample loss to a minimum where available analyte quantity is very limited and where convenience of measurement is desired.

Prior art concentrates on the containment of samples in vessels or containers wherein the sample volume is usually from 20 to 1000 microliters. A relatively straightforward spectrofluorometer design can be seen in Nogami et al. U.S. Pat. No. 5,500,536. A spectrofluorometer utilizing simultaneous multiple source wavelengths can be seen in Goldstein U.S. Pat. No. 5,422,719. Use of optical fibers in the spectrofluorometer optical system can be seen in Glebeler et al. U.S. Pat. No. 6,313,471. A good general introduction to fluorescence can be found in "Principles of Fluorescence Spectroscopy" by Joseph R. Lakowitz, 1999, Kluwer Academic/Plenum Publishers, 233 Spring Street, New York, N.Y., 10013, pages 1 to 9.

Robertson, in U.S. Pat. Nos. 6,628,382 and 6,809,826 discloses method and apparatus for photometric or spectrophotometric measurements on extremely small samples. These "nanodrop" samples, as they are termed therein and herein, are on the order of 2 microliters or less and are contained by surface tension. These patents are incorporated in their entirety by reference. In the apparatus of Robertson, a nanodrop is contained by surface tension between two relatively moveable, substantially parallel surfaces, "anvils", which are moved together after the sample is loaded upon one of them in order to wet both surfaces. The anvils are then moved apart to draw the droplet into a column to establish an optical path through the length of which light is projected. In-line optics are used to pass light through the column. The light passes from an input optical fiber in one anvil to an aligned output optical fiber in the other and to a sensor, a charge coupled device or the like, which can be part of a spectrometer or other optical detection system, where a photometric or spectrophotometric measurement is made.

In U.S. Pat. No. 6,809,826, Robertson discloses an improved version of the above invention in which the wetted surface area on the anvils is limited by various means.

In these two patents Robertson teaches that fluorescence may be measured with the apparatus disclosed therein.

Measurements of the type disclosed in the referenced Robertson patents, however, are not optimally applicable to measurement of a fluorescing nanodrop. Containing the sample by surface tension is appropriate and highly effective. However the light handling system of the two, prior-art, Robertson inventions tends to overwhelm a fluoroscopic measurement particularly so when a weakly emitting or fluorescing sample is involved. Light used to excite the fluorescence projected from one in-line optical fiber through the drawn column of fluid to excite fluorescence in the contained nanodrop and directly into an in-line receiving optical fiber to a sensor interferes with the much less intense light produced by the sample fluorescence itself. In addition, fluorescence from the optical fibers would be high for some exciting wavelengths.

It is therefore an object of this invention to provide method and apparatus for performing fluorescence measurements on nanodrops contained by surface tension wherein transmittance of emitted fluorescent light received by the sensing system is maximized and light from other sources, ambient illumination, fluorescence from the system optical fibers and particularly scattered light from the exciting source, that is received by the sensing system is minimized.

It is a further object of this invention to provide method and apparatus for the measurement of fluorescence wherein a nanodrop sample is contained by surface tension and the exciting light, and any stray ambient light is substantially barred from the measuring detection system.

It is a still further object of this invention to provide method and apparatus for the measurement of fluorescence emitted by a nanodrop sample contained by surface tension wherein compensation is substantially provided for any exciting and ambient light that does impinge on the measuring sensor.

BRIEF DESCRIPTION OF THE INVENTION

The objects of the invention are met by apparatus for measuring fluorescence of a sample in the form of a liquid drop contained by surface tension forces in a containment area between two anvil surfaces in a substantial parallel relationship, an optical path having been established between wetted areas on each of the two surfaces through the wetting sample drop. The apparatus comprises:

first and second anvil surfaces at least one being moveable relative to the other to any one of three positions;

an adjustable sample loading position so selected that the surfaces are opposed and substantially parallel and proximally spaced so that the liquid spreads upon both surfaces forming a wetted area on each of the at least one moveable surface and the other surface are so remotely spaced that a droplet can be placed on the first surface;

an adjustable compression position so selected that the anvil surfaces are opposed and substantially parallel and proximally spaced so that the liquid spreads upon both surfaces forming a wetted area on each;

an adjustable sample measuring position so selected that the opposed substantially parallel surfaces are spaced apart to pull the sample into a column wherein it is contained by surface tension thereby providing an optical path for a measurement of fluorescence; plus an open position where the sample surfaces are sufficiently far enough apart to allow both surfaces to be wiped or cleaned by other means to remove the sample and any associated residue;

one anvil surface having the proximal end of a first multimode optical fiber flush with the surface thereof within the wetted area and of a selected transmission numerical aperture (for an explanation of numeric aperture see *Fundamentals of Optics* by Francis A. Jenkins and Harvey E. White, McGraw-Hill, 1957, page 307) to minimize any off axis, or high numeric aperture excitation or ambient light, the distal end of the first fiber in active connection with a spectrometer or other detector capable of sufficient wavelength discrimination so as to make a good fluorescence detector;

the other anvil surface containing a signal-modifying means comprising a second optical fiber having its proximal end finished flush with the surface thereof within the wetted area and of selected transmission numerical aperture, the distal end of the second fiber having means for signal modification;

means for illuminating the sample comprising a relatively collimated light from at least one source located away from the sample containment area illuminating the sample from the side such that minimal light enters the optical fibers within their selected numeric apertures, the source having a stable wavelength intensity distribution.

A preferred embodiment of the method of operating the apparatus includes compensation for any exciting and ambient light that does impinge on the measuring sensor. This is accomplished by removing instrumentation and background contributions from the signal by separately measuring them and subtracting their spectra from the sample measurement spectrum. The very high rejection multimode optical fibers have for light incident at angles significantly above the angle of the optical fiber transmission numerical aperture and the reduction in scattering as a result of wetting or optical contact of all optical surfaces associated with the sample measurement is sufficient to reduce the background light from the source to a level where it is feasible to extract the fluorescence by simply subtracting a scaled representation of the source, the principle improvement which is being called virtual filtering.

This is a method that involves the steps of:
i. recording the source spectrum using a sample with no fluorescence;
ii. selecting at least one fluorescing target and incorporating that target in a sample;
iii. selecting a default wavelength interval encompassing all or most of the fluorescence emission wavelengths;
iv. measuring the fluorescence of said sample with a spectrometer;
v. outputting the measurement of step iv to a programmed means for calculation;
vi. calculating the respective fluorescence of the sample by scaling the recorded source spectrum to match the intensity of the sample at a wavelength where the fluorescence signal is known to be 5% or less of peak fluorescence, typically on the short wavelength side of the fluorescence peak;
vii. subtracting the scaled source spectrum from the signal spectrum containing some scattered source radiation as well as the fluorescence signal; and
viii. displaying the resulting signal spectrum.

A preferred embodiment of virtual filtering, especially for lower signal fluorescent samples, involves the use of a wavelength interval encompassing most of the fluorescence signal, typically, but not necessarily symmetrical about the peak fluorescence value over which to scale the recorded source spectrum for subtraction from the total signal.

This method involves the steps of:
i. recording the source spectrum using a sample with no fluorescence;
ii. selecting at least one fluorescing target and incorporating that target in a sample;
iii. selecting a default wavelength interval encompassing all or most of the fluorescence emission wavelengths;
iv. measuring the fluorescence of said sample with a spectrometer;
v. outputting the measurement of step iv to a programmed means for calculation;
vi. calculating the respective fluorescence of the sample by independently scaling the previously recorded source spectrum to match the sample spectrum at specific intervals about the emission wavelength selected and linearly interpolating between those values;
vii. subtracting the scaled source spectrum from the signal spectrum containing some scattered source radiation as well as the fluorescence signal setting all values of the fluorescence signal outside the fluorescence emission range to zero; and
viii. displaying the resulting signal spectrum.

Alternatively, a filter that passes only excitation light can be inserted between the source and the sample and a filter that passes only the fluorescence from the sample placed between the sample and the detector. Thus fluorescence from the sample can be detected but any scattered light from the source is rejected by the filter. Most illuminating sources have some output intensity at the same wavelengths as the fluorescence and these can be minimized by use of the above mentioned blocking filter.

The means for signal modification provided at the distal end of the second fiber can vary from signal gain to nearly complete damping of the signal in that optical fiber. In the former instance a mirrored surface cap is provided at the end of the fiber. This has the effect of returning the fluorescent emission in the fiber to be transmitted back through the sample to the sensor. In most instances of practical use, it has been found that such a configuration tends also to increase unwanted ambient and background excitation light energy. The other instance employs means to form an energy-absorbing surface to minimize transmission of unwanted light to the measuring sensor. Drawing the fiber to a long thin point can do this, as can ending the fiber with or into an absorbing coating or surface or making the fiber using a glass that is highly absorbing throughout the fluorescence and excitation wavelength range.

DETAILED DESCRIPTION OF THE INVENTION

Using the system for sample containment disclosed by Robertson, it is possible to make good fluorescence measurements on otherwise clear samples with a minimum of filtering optics. The very high rejection multimode optical fibers have for light at angles significantly greater than the angle of the fiber transmission numeric aperture and the total wetting or optical contact of all surfaces associated with the sample measurement is sufficient to reduce the background light from the source to a level where it is feasible to extract the fluorescence by simply subtracting a scaled representation of the source. An additional element in making this feasible is the high reproducibility of the spectral output relative intensity vs. wavelength of solid-state light emitting diodes (LEDs). A diagram showing the illumination geometry is shown as FIG. 1.

Figures 1, 1A:
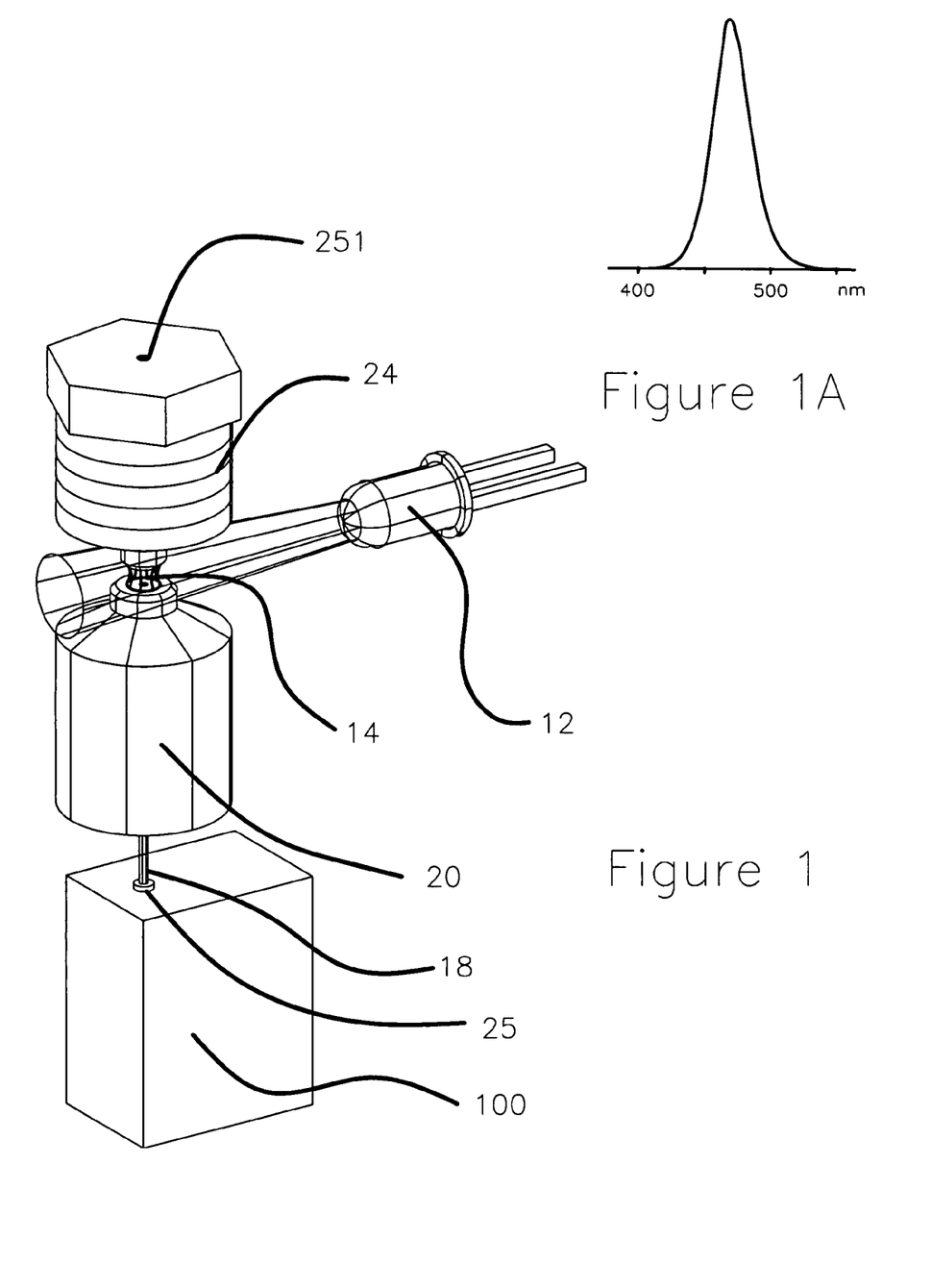
FIG. 1 is a schematic drawing of the mode of fluorescence excitation and detection employed.
FIG. 1A is the output intensity spectrum of a blue LED used in one embodiment of the invention.

In FIG. 1 the exciting LED 12 is shown illuminating the liquid sample column 14. In the apparatus, it is preferred to use at least one and preferably three LEDs to provide excitation energy over the wavelength range needed to excite most commonly used fluorescent materials. The light from at least one LED 12 excites fluorescence in the molecules of interest in the sample 14. The fiber 18 seen below anvil 20 carries the light from the fluorescing sample to a fiber optic spectrometer 100. Fiber 18 extends through anvil 20 and is finished flush with its surface so that the sample can wet it. An opposing somewhat larger optical fiber or rod 251 in anvil 24 not fully seen in this view but shown in the cross-section of FIG. 7, has a mirror or light sink 28 at its opposing end or the fiber is made from an absorbing glass material. A mirror reflects more of the sample light into the spectrometer fiber. A light sink reflects less of the sample light and less of the interfering light. The absorbing glass should return no excitation or fluorescence light to the detection system through fiber 18.

In order to extract the source spectrum from the light signal coming from the sample, the source spectrum is mapped using the stray light from a sample with no fluorescence to record the relative intensity spectrum of the source. A diagram of one mode of sample processing is shown in FIG. 2.

Figure 2:
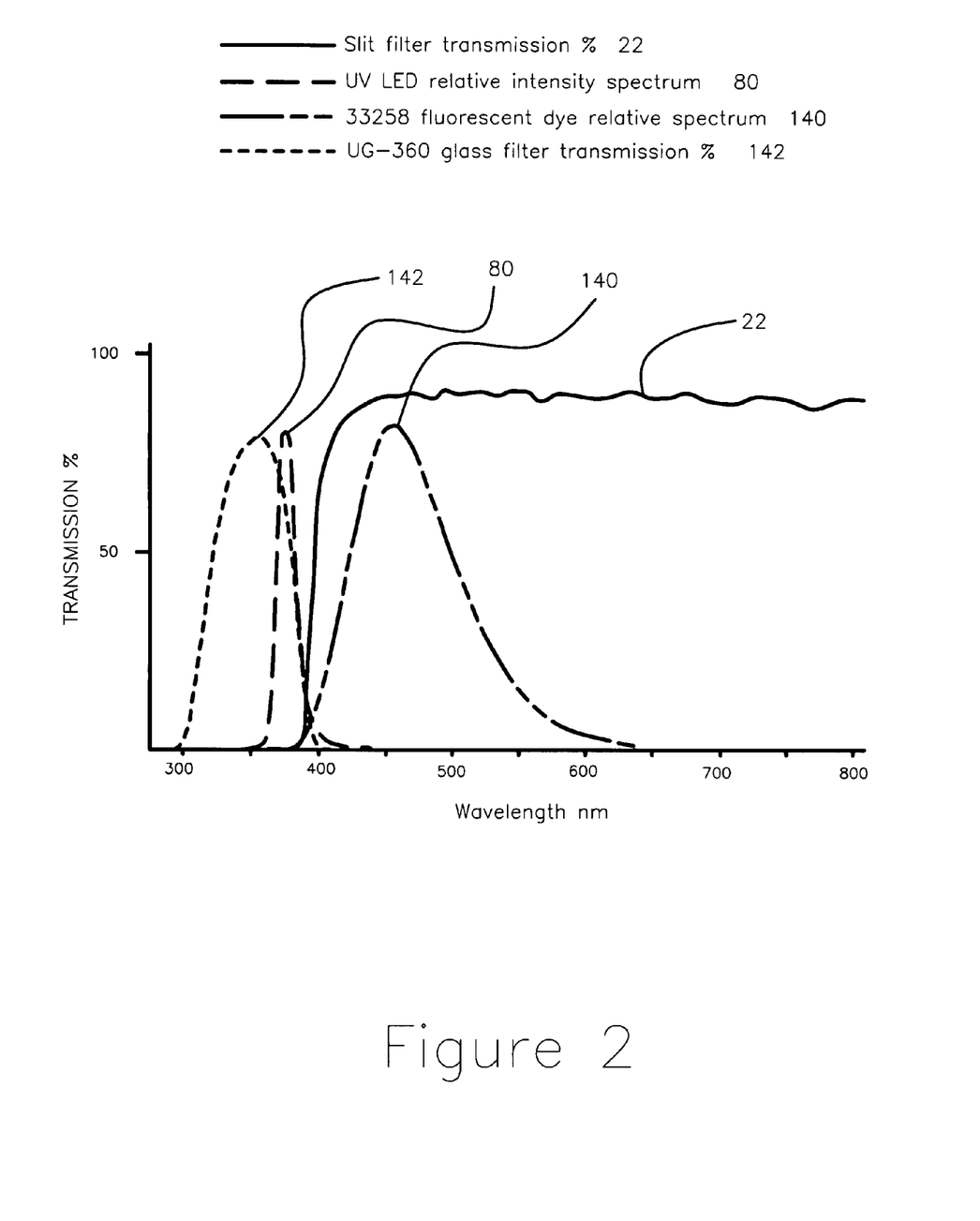
FIG. 2 diagrams the method for extracting fluorescence signals from fluorescent dyes that use UV LED excitation.
Figure 8:
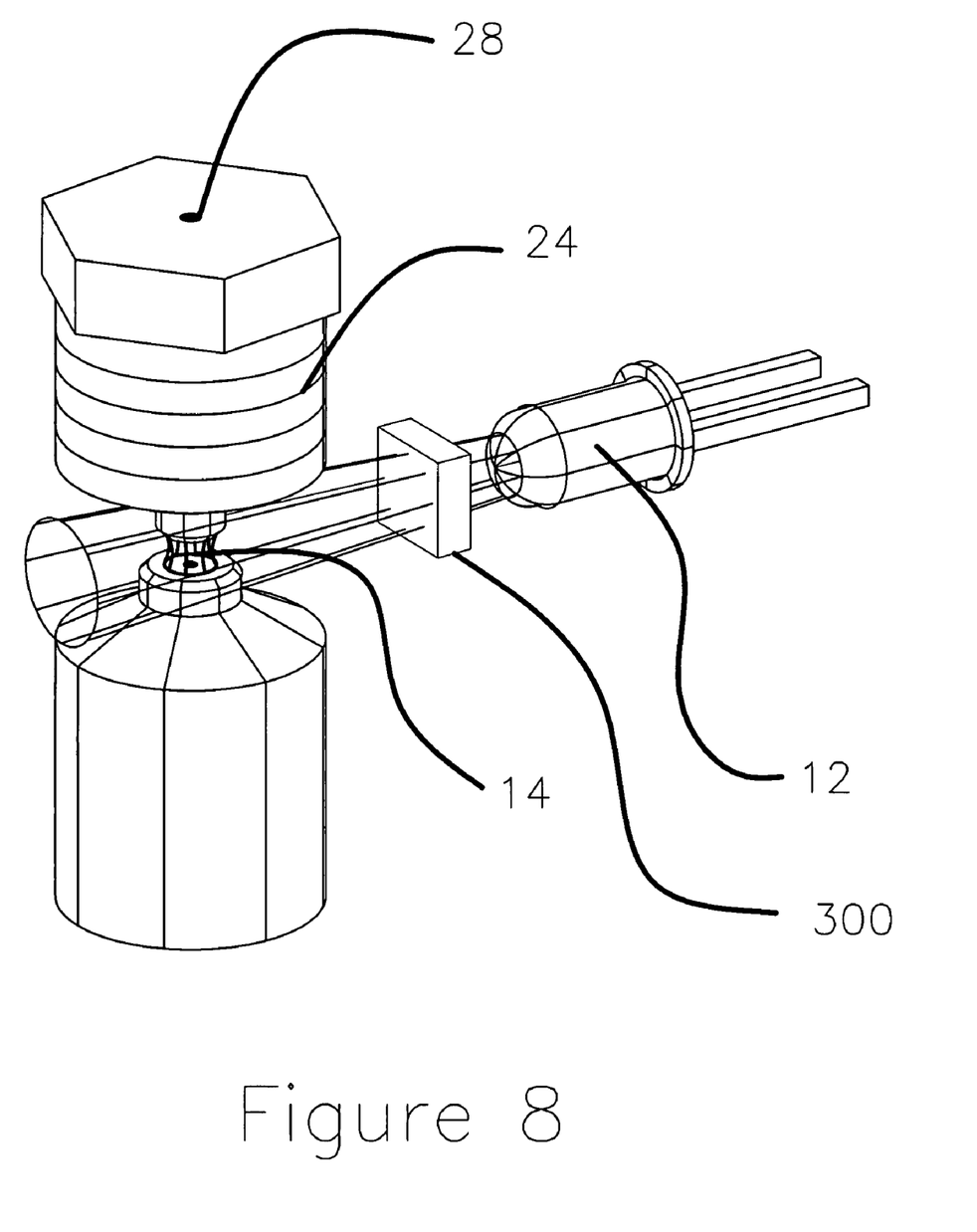
FIG. 8 shows the illumination system with a source filter between the LED and the sample.

FIG. 2 shows the process used to extract the fluorescence spectrum from the sample in the instrument illuminated, for example, by a relatively monochromatic UV LED (e.g. Nichia Chemical Co. p/n NSHU590B). Signal from the exciting LED in the wavelength range of the fluorescence of the Hoechst 33258 fluorescent dye 140 of FIG. 2 is blocked by the Hoya UG-360 ultraviolet glass filter whose transmission is shown as 142 of FIG. 2 placed between the LED and the sample as is shown in 300 of FIG. 8 and an interference filter whose transmission spectrum 22 allows the fluorescence of the 33258 dye to pass but blocks the excitation light from the LED passed by the UG-360 filter as is shown in FIG. 2 placed at the slit of the spectrometer shown as 25 in FIG. 1. Thus light at the peak wavelength of the 33258 dye is not interfered with by light from the source and light from external sources can be subtracted by measurement of light coming from the sample with the source LED turned off. Similar filter use can be used to block excitation light from other LEDs used as fluorescence excitation sources, but the filter at the spectrometer slit ultimately limits the range of fluorescence that can be measured in a given instrument configuration.

Figure 3:
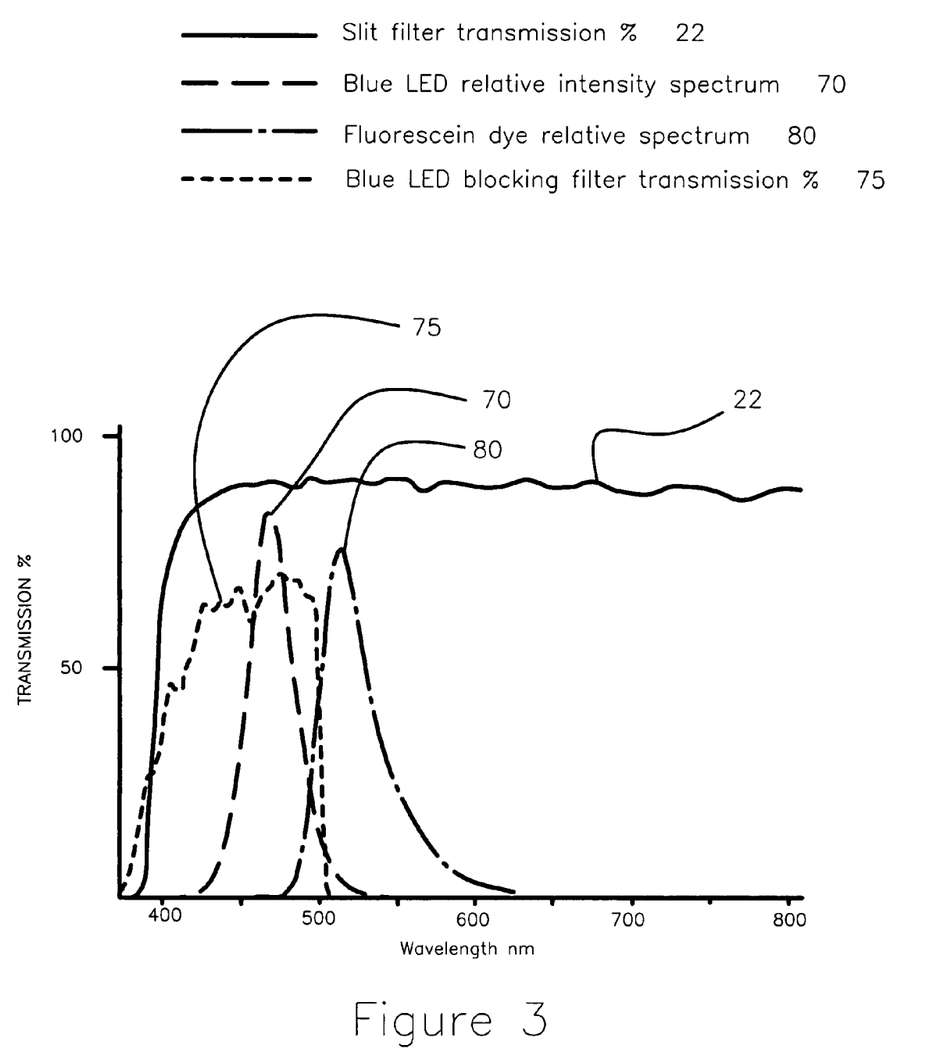
FIG. 3 diagrams the method for extracting fluorescence signals from fluorescent dyes that use blue LED excitation.

FIG. 3 shows the method for extracting signal information from fluorophores using LEDs emitting light in the range of visible wavelengths such as a blue LED having the spectrum of FIG. 1A. In this case the interfering part of the output intensity spectrum of a blue LED shown as 70 is blocked by a filter with a transmission curve shown as 75 placed between the LED and the sample in a fashion similar to that of the UV filter 300 of FIG. 8. The fluorescence emission intensity spectrum shown as 80 in FIG. 3 is thus not interfered with by light from the LED or the slit filter transmission shown as 22.

Figure 4:
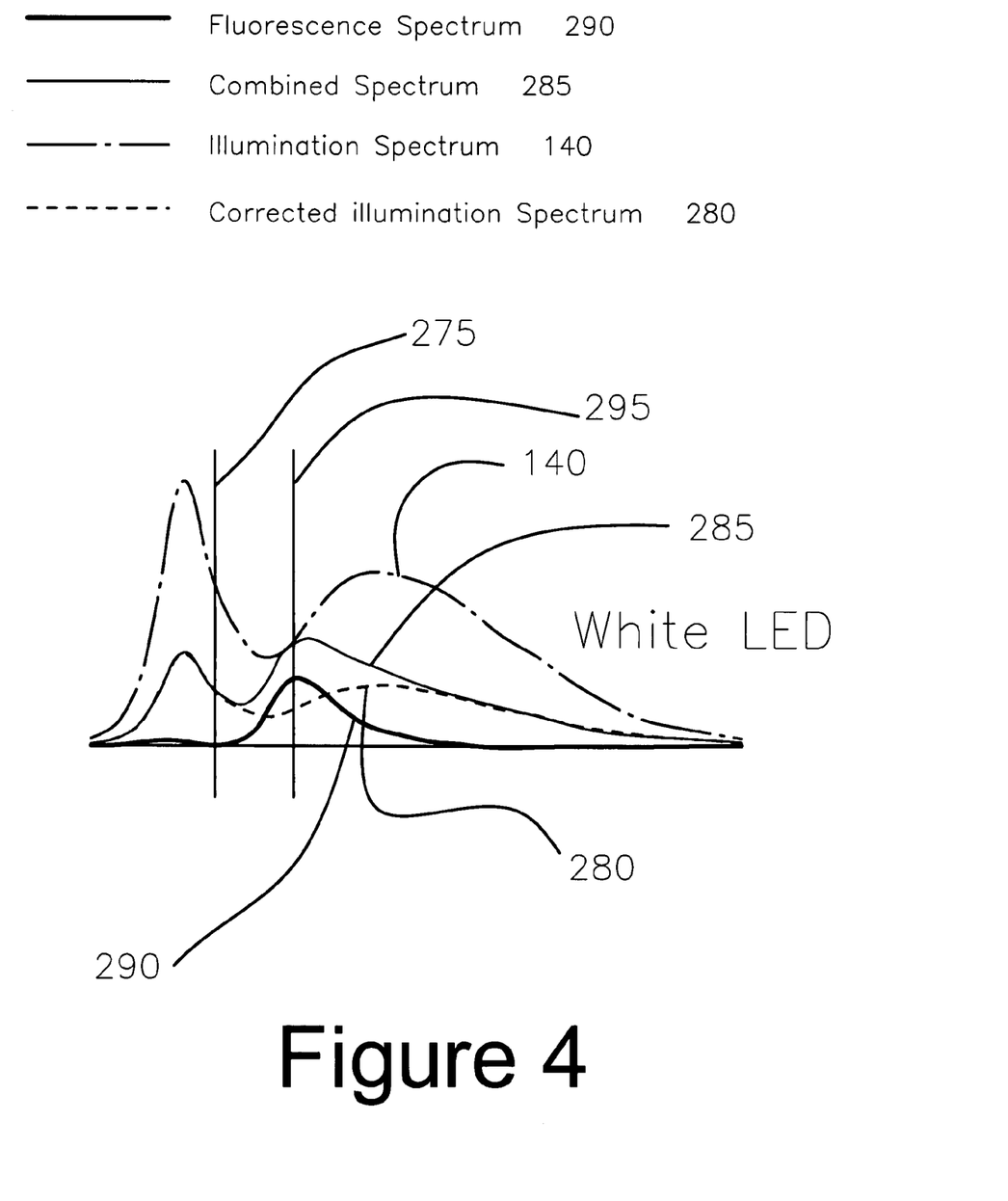
FIG. 4 is a diagram of how the fluorescence spectrum is extracted from the signal received by the spectrometer from the sample using "reference wavelength" virtual filtering and white LED excitation.
Figure 7:
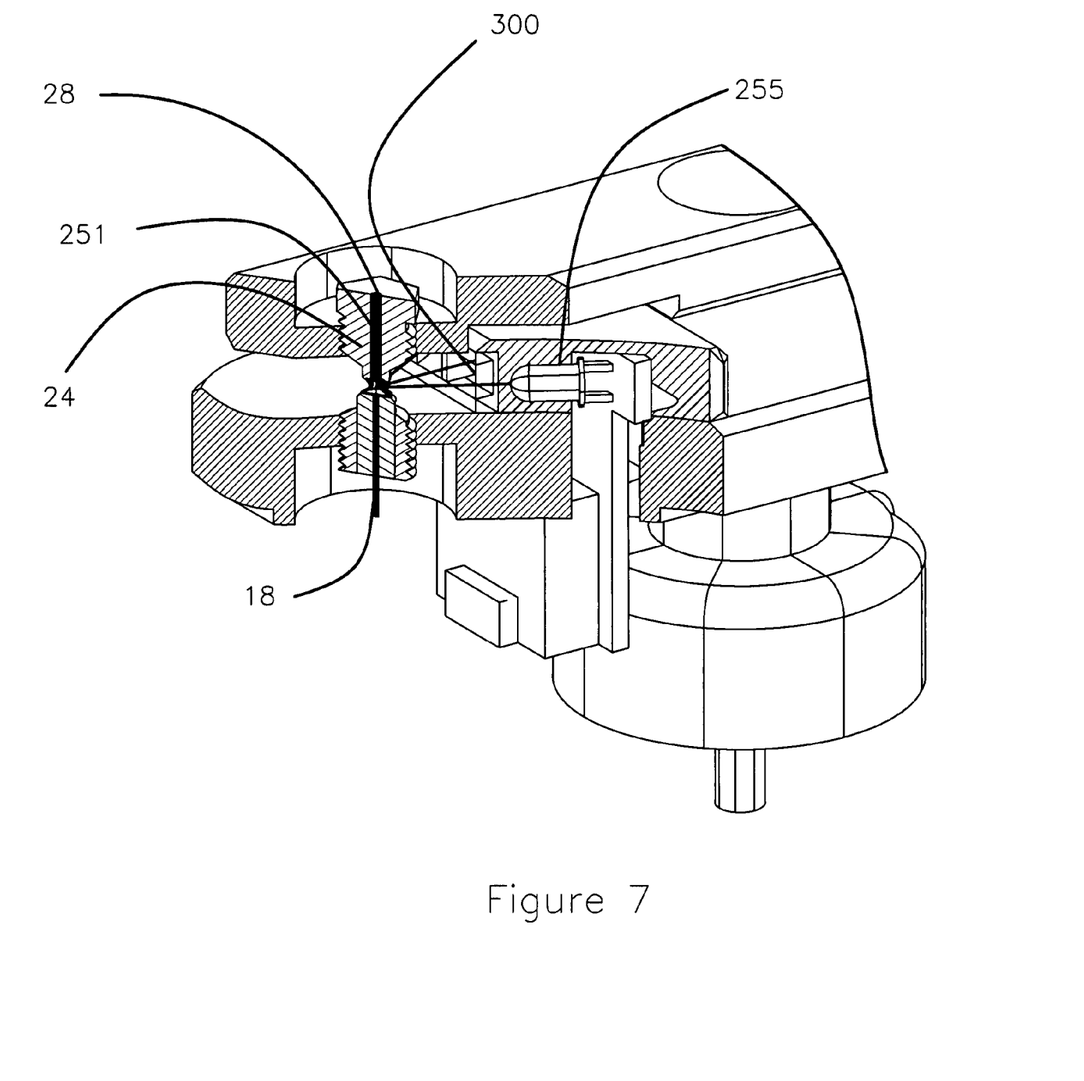
FIG. 7 is an enlargement of the cross-section of FIG. 6 showing the arrangement of the illuminating LEDs.

In the most general case, where the excitation comes from a broad spectrum source such as a white LED, using no filter between the LED and the sample as is shown with LED 255 in FIG. 7, the fluorescence of the sample can be measured by virtual filtering shown in FIG. 4. To do this, the spectrum of the source, typically a white LED whose intensity spectrum, i.e. illumination, is shown as 140 in FIG. 4 is scaled and removed as follows: for each emission maximum (wavelength shown for fluorescein in FIG. 4 as 295) selected, software automatically chooses a default or reference wavelength shown as 275 in FIG. 4. The source spectrum is scaled so that the intensities match at the default wavelength. This scaled or corrected source spectrum shown as 280 in FIG. 4 is subtracted from the signal spectrum 285 to yield a spectrum of fluorescence intensities and the fluorescence intensity is measured at the fluorescence peak shown as 295 in FIG. 4.

Figure 9A:
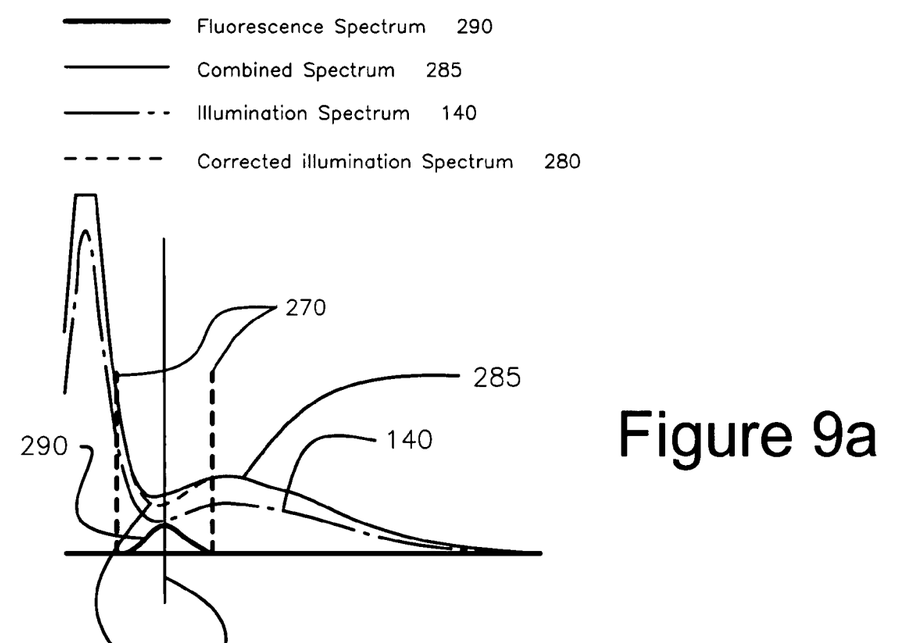
FIGS. 9a and 9b show the preferred embodiment of virtual filtering using 2 wavelength background removal.
Figure 9B:
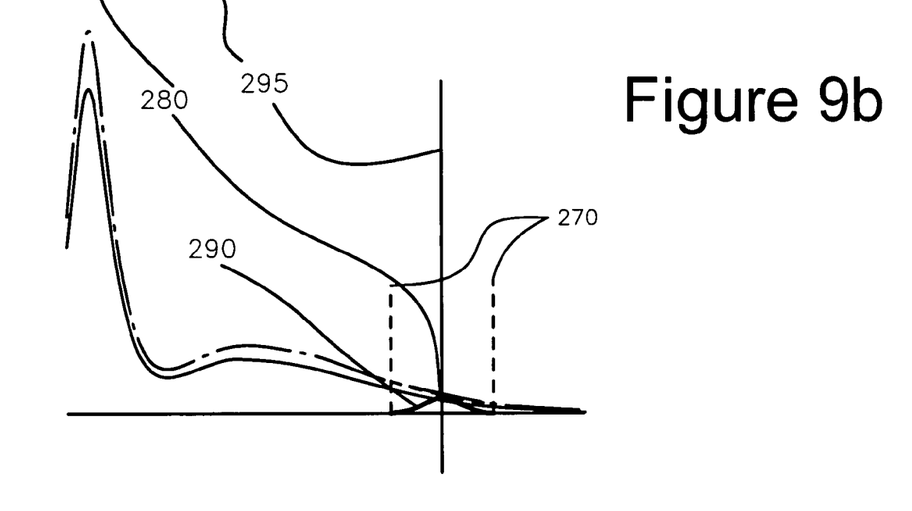

In the preferred embodiment for low fluorescence signals, where the excitation comes from a broad spectrum source such as a white LED, using no filter between the LED and the sample as is shown with LED 255 in FIG. 7, the fluorescence of the sample can be measured by virtual filtering shown in FIGS. 9a and 9b. To do this, the spectrum of the source, typically a white LED whose intensity spectrum, i.e. illumination, is shown as 140 in FIGS. 9a and 9b is scaled and removed as follows:

i. For each emission maximum wavelength shown for fluorescein in FIG. 9a and Alexa 647 in FIG. 9b as 295, the software automatically incorporates a default wavelength interval shown as 270 and extending 30 nm each side of the maximum wavelength 295 in FIGS. 9a and 9b, the Virtual Emission Filtering Interval (D1)—which is currently, AND ARBITRARILY, symmetrically applied but need not be. This scaled or corrected source spectrum is shown as 280 in FIG. 9b and the intensity is measured at the fluorescence peak shown as 295 in FIG. 4. The configurable reference wavelength interval $\Delta\lambda$, with a SELECTED default setting of ±20 nm is the respective wavelength range over which the residual sample fluorescence signal (with scaled, stable source spectrum subtracted), is displayed.

ii. Over the interval D1 the source spectrum is scaled by scaling the intensity values at the end wavelengths of the interval to match the corresponding values in the sample spectrum and setting intermediate values using linear interpolation between the interval ends of D1.

iii. The scaled source spectrum is then subtracted from the sample spectrum leaving the intensities of the fluorescence spectrum.

For visualization purposes, the signal outside the virtual filtering interval is set to zero (0) as is shown in FIGS. 9a and 9b. In the case of unfiltered broad spectrum excitation like the white LED, the measured signal of low level fluorescence is much more dependent on the accuracy in taking the difference of two relatively large numbers representing the source and the source contribution to the signal spectrum to extract the low level fluorescence signal from its background. The virtual emission filtering interval significantly improves the ability to measure the lowest levels of sample fluorescence. These practices make it possible to excite the fluorescence of a broad range of fluorophores using the broad-spectrum source and detect sufficient signal to be useful for many fluorescence measurements. Since most fluorescence measurements are made by comparing unknown samples with standards, the measurements are not significantly distorted by the small amount of lost signal beyond the ends of the virtual filtering interval as the same proportional signal is lost from the standards. Users may selectably display all spectra used in the virtual filtering process for verification of the proper function of the process.

Figure 5A:
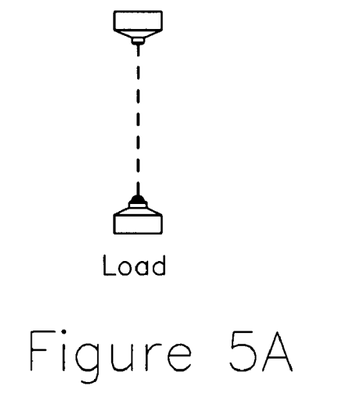
FIGS. 5a, 5b, and 5c show the prior art steps of how a sample is loaded into the apparatus, compressed to wet both anvil surfaces, and then stretched into a column for measurement.
Figure 5B:
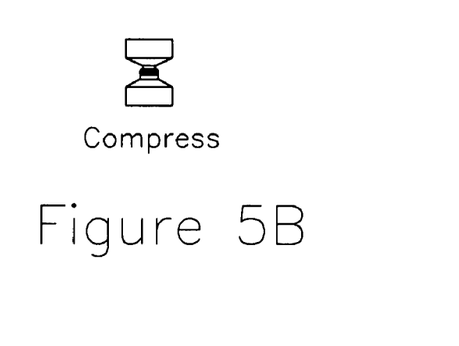
Figure 5C:
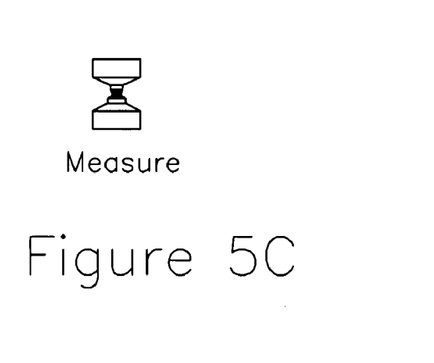

In order to load the sample into the instrument, the sample is placed on one of the optic tips as shown in FIG. 5A, following the method taught in the Robertson patents previously mentioned, using a small volume laboratory pipetter. The sample is then contacted by the opposing fiber optic tip and compressed to wet both tips, FIG. 5B, causing the sample to center in the measurement zone and form a measurement column when the upper tip returns to its measurement position as can be seen in FIG. 5C. The method of operation shown diagrammatically in FIGS. 5A, 5B and 5C is the prior art containment apparatus and method disclosed in the referenced Robertson patents and shows the prior art containment apparatus.

Figure 6:
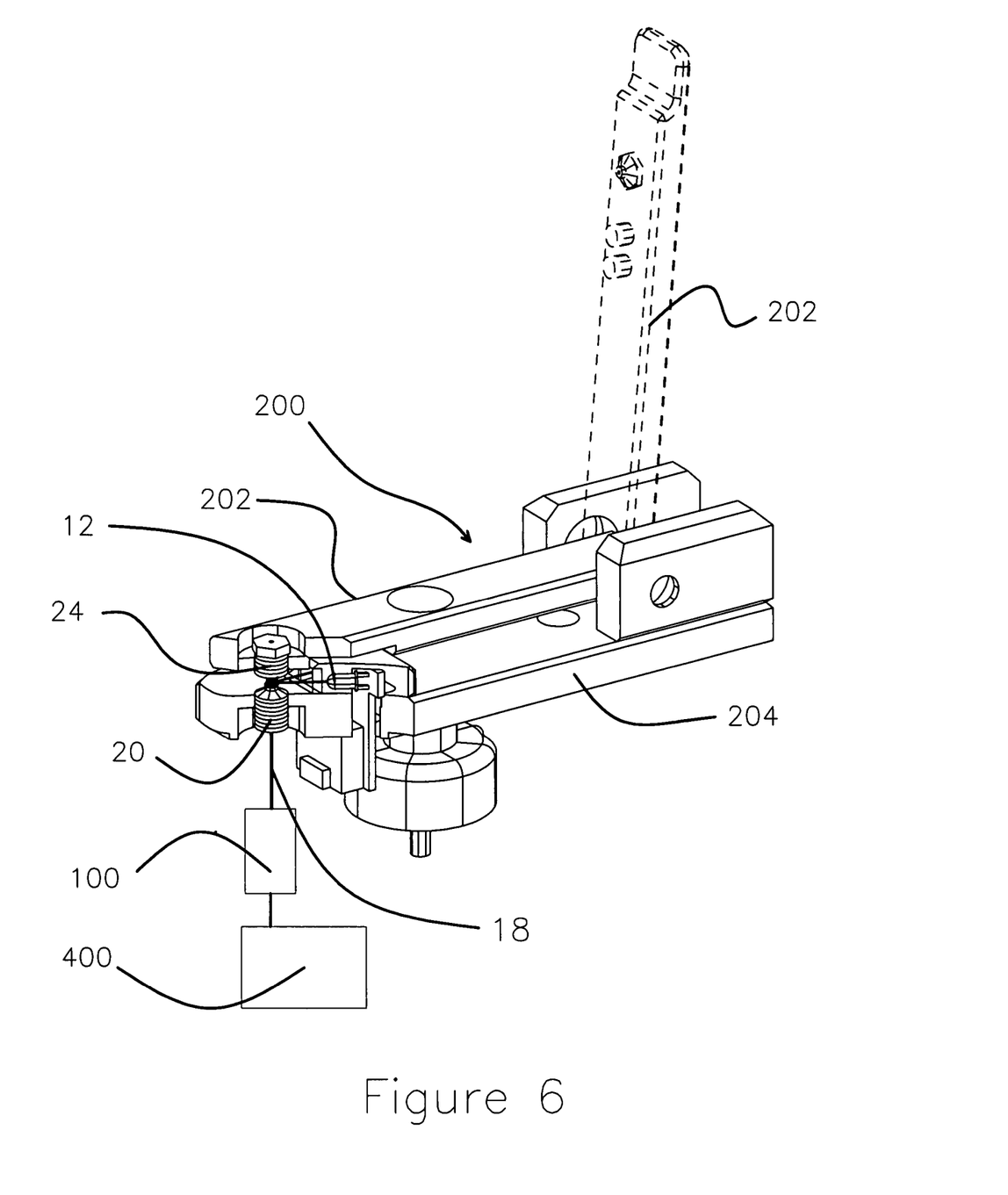
FIG. 6 shows in phantom lines the apparatus for handling the sample in the open loading position and in solid lines, the closed measurement position partially cross-sectioned.

The apparatus 200 for making measurements using a swinging arm 202 to accommodate loading and cleaning after sample processing is shown in FIG. 6. Arm 202 is pivotally mounted to frame 204, a fixed arm, each arm respectively holding anvils 24 and 20. The sample is illuminated from the side by one or more LEDs 12 in the apparatus. Three or more LEDs are preferred. A solenoid below accomplishes the controlled compression and forming of the measurement column by allowing the arm to move to a lower position during the compression phase and return it to the measurement position afterwards. This measurement geometry is shown in FIGS. 6 and 7 where the signal from the measurement column is carried directly to the entrance slit of a fiber optic spectrometer 100, FIG. 1 by optical fiber 18 shown in FIGS. 1, 6, 7 and 8. An enlarged view of the sample measurement region of the instrument is shown in FIG. 7. This system has been demonstrated to be capable of detecting less than 1 femtomole of sodium fluorescein in TE buffer in a 1 microliter sample (a 1 nanomolar solution) using a 470 nm blue LED, p/n E482 from Gilway Technical Lamp of 55 Commerce Way, Wobum Massachusetts 01801-1005, a 400 micron multimode fiber with SMA terminations from RoMack inc. of 5583 Mooretown Rd. Williamsburg, Va. 23188 and a fiber optic spectrometer p/n USB2000-FL from Ocean Optics of 830 Douglas Ave, Dunedin, Fla. 34698.

To perform virtual filtering measurements spectra are outputted from spectrometer 100 to a computer 400 wherein the virtual filtering steps described above are performed.

EXAMPLE 1

Figure 10:
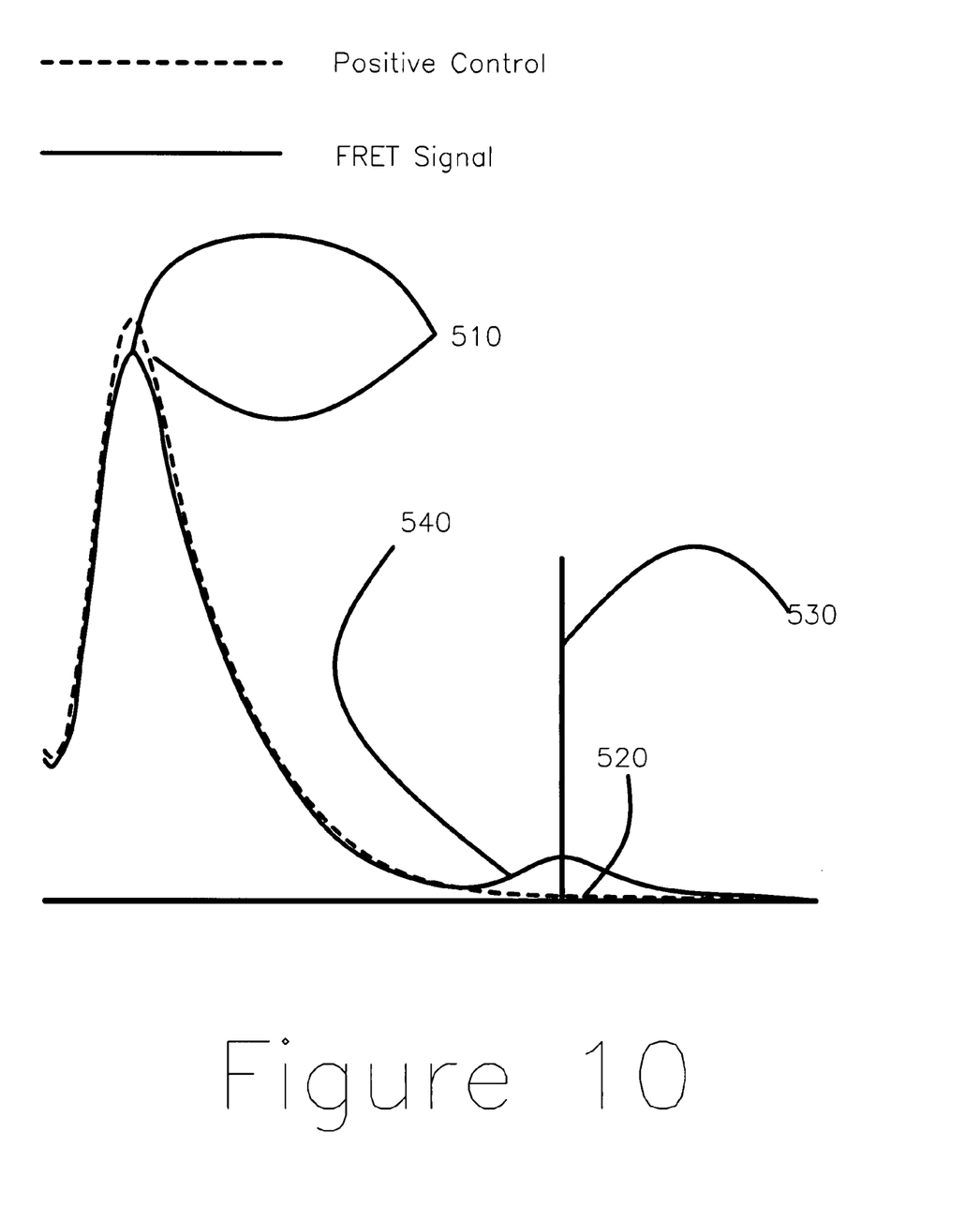
FIG. 10 shows the emission spectra of a donor—acceptor FRET pair and its positive control.

Emission Spectra of a Donor—Acceptor FRET (Fluorescence Resonance Energy Transfer) Pair and its Positive Control The FRET pair was constrained in a hairpin configuration comprised of a single-stranded nucleotide probe (loop) and a double-stranded nucleotide (stem) structure. The fluorescence donor (fluorescein) was covalently attached at one end and an acceptor (Cy5) covalently attached to the other end of the stem. Thus, In the absence of the complimentary nucleotide sequence to the probe (loop), the hairpin's double-stranded (base-paired) stem structure is conserved. The excited donor's fluorescence 510 was proportionally transferred to the acceptor resulting in longer wavelength fluorescence emission 540 at wavelength 530. In the presence of the complimentary sequence to the single-stranded probe (loop), the hairpin's base-paired stem structure was disrupted, double-stranded probe was formed, and the resonance energy from the excited donor 510 was not transferred 520 to the acceptor at wavelength 530. The positive control was spectrally distinguished by reduction or elimination of the acceptor's longer wavelength emission 520 at wavelength 530.

EXAMPLE 2

Figure 11:
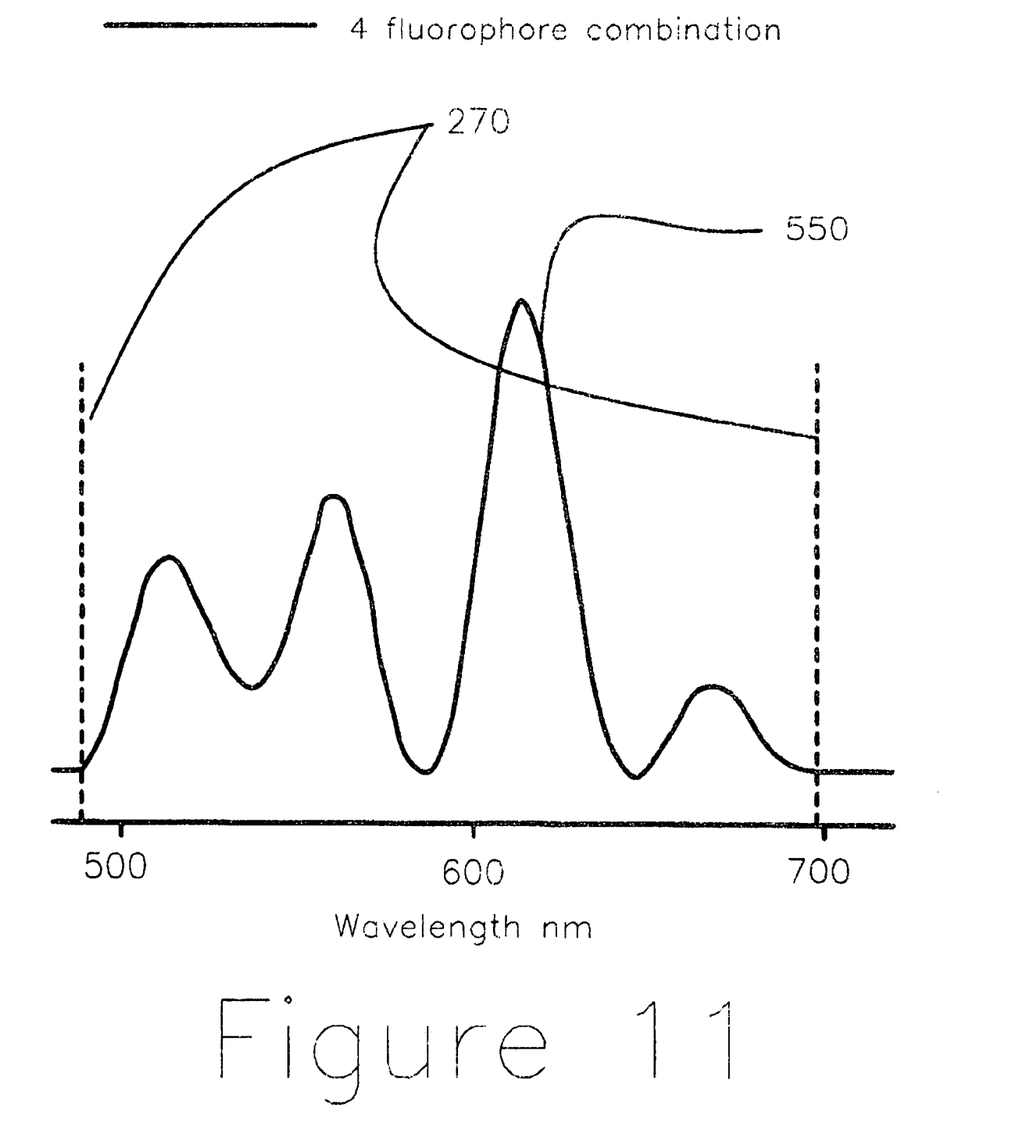
FIG. 11 shows the virtual-filtered emission spectrum of a solution containing four fluorophores excited with an unfiltered white LED.

Virtual-filtered Emission Spectrum of a Solution Containing Four Fluorophores Excited with an Unfiltered White LED Complex mixtures of fluorophores having excitation maxima differing by 200 nm have been excited using a single broad wavelength unfiltered white LED source, shown as 140 in FIG. 4. The resulting virtual-filtered emission spectrum of four fluorophores, each differing by approximately 50 nm within the wavelength boundary 270, was displayed and labeled as 550.

We claim:

1. Apparatus for the measurement of fluorescence of a fluorescently-excited sample in the form of a fluorescently-excited liquid drop contained by surface tension forces between two anvil surfaces in a substantially parallel relationship, an optical path having been established between wetted areas on each of the two surfaces, said apparatus comprising:

first and second substantially parallel anvil surfaces, one being moveable relative to the other to any one of three positions;

an adjustable sample loading position so selected that at least one moveable surface and the other surface are so remotely spaced that a droplet can be placed on the first surface;

an adjustable compression position so selected that the anvil surfaces are opposed and substantially parallel and proximally spaced so that the liquid spreads upon both surfaces forming a wetted area on each;

an adjustable sample measuring position so selected that the opposed substantially parallel surfaces are spaced apart to pull the sample into a column wherein it is contained by surface tension thereby providing an optical path for a measurement of fluorescence;

one said anvil surface having the proximal end of a first optical fiber flush with the surface thereof within said wetted area, the distal end of said first optical fiber in active connection with a spectrometer detector;

the other said anvil surface having the proximal end of a second optical fiber in-line with said first optical fiber flush with the surface thereof within said wetted area, the distal ends of second optical fiber having means for modifying the optical signal transmitted within said optical fiber;

at least one means for illuminating the sample comprising a relatively collimated light such that minimal light enters the optical fibers within their transmission numeric aperture from at least one source located away from the sample containment area, said source having a stable wavelength distribution of selected extent to excite the fluorescence of target molecules in said sample.

2. Apparatus as in claim 1 wherein fluorescent light from the sample is conveyed by means of an optical fiber to a detector.

3. The apparatus of claim 1 wherein the signal modifying means comprises a mirrored cap whereby the fluorescence signal to said fluorometer is enhanced.

4. The apparatus of claim 1 wherein the signal modifying means comprises an optical sink whereby the signal from exciting and ambient light transmitted to said fluorometer is minimized.

5. The apparatus of claim 1 wherein the signal modifying means comprises an absorbing optical fiber or rod whereby the signal from exciting and ambient light transmitted to said fluorometer is minimized.

6. The apparatus of claim 1 wherein at least one means for illuminating said sample is a blue LED.

7. The apparatus of claim 1 wherein at least one means for illuminating said sample is a white LED.

8. The apparatus of claim 1 wherein at least one means for illuminating said sample is an ultraviolet LED.

9. The apparatus of claim 1 wherein there are at least three means for illuminating said sample.

10. A method for measuring the fluorescence of a liquid nanodrop sample contained by surface tension between two substantially parallel anvil surfaces of the apparatus of claim 4 comprising:
    opening said apparatus to said sample loading position;
    loading said nanodrop onto one said anvil surface;
    closing said apparatus to said sample compression position;
    opening said apparatus to said sample measuring position;
    Illuminating said sample with said excitation light;
    measuring any emitted fluorescence from said sample to obtain a sample spectrum.

11. The method of claim 9 wherein the sample is a nanodrop confined by surface tension.

12. The method of claim 9 wherein there are more than one fluorescing targets.

13. The method of claim 9 wherein the default wavelength interval that is selected ranges between 20 and 40 nanometers.

14. A method for measuring the fluorescence spectrum of a sample subjected to light from a source comprising subtracting a scaled source spectrum from said measured sample spectrum to obtain the sample fluorescence spectrum comprising the steps of:
    i. recording the source spectrum using a sample with no fluorescence;
    ii. selecting at least one fluorescing target and incorporating that target in a sample;
    iii. selecting a default wavelength interval encompassing all or most of the fluorescence emission wavelengths;
    iv. measuring the fluorescence of said sample with a spectrometer;
    v. outputting the measurement of step iv to a programmed means for calculation;
    vi. calculating the respective fluorescence of the sample by scaling the recorded source spectrum to match the intensities outside the fluorescence emission wavelength range as best possible;
    vii. subtracting the scaled source spectrum from the signal spectrum containing some scattered source radiation as well as the fluorescence signal; and
    viii. displaying the resulting signal spectrum.

\* \* \* \* \*